US011001353B2

(12) United States Patent
Sunol et al.

(10) Patent No.: US 11,001,353 B2
(45) Date of Patent: May 11, 2021

(54) GAS-INFLATABLE PERSONAL FLOTATION DEVICES

(71) Applicants: Aydin Kemal Sunol, Tampa, FL (US); Evan James Ticknor, Kissimmee, FL (US); Selina Kyle Guardiano, Port Orange, FL (US); Timothy Warren Jacobson, Jensen Beach, FL (US); Everett David Rogers, Largo, FL (US); Kyle Louis Cogswell, Tampa, FL (US); Robert Dana Frisina, Tampa, FL (US); Christopher Lawrence Passaglia, Lutz, GA (US)

(72) Inventors: Aydin Kemal Sunol, Tampa, FL (US); Evan James Ticknor, Kissimmee, FL (US); Selina Kyle Guardiano, Port Orange, FL (US); Timothy Warren Jacobson, Jensen Beach, FL (US); Everett David Rogers, Largo, FL (US); Kyle Louis Cogswell, Tampa, FL (US); Robert Dana Frisina, Tampa, FL (US); Christopher Lawrence Passaglia, Lutz, GA (US)

(73) Assignee: University of South Florida, Tampa, FL (US)

( * ) Notice: Subject to any disclaimer, the term of this patent is extended or adjusted under 35 U.S.C. 154(b) by 69 days.

(21) Appl. No.: 16/520,581

(22) Filed: Jul. 24, 2019

(65) Prior Publication Data
US 2019/0344867 A1 Nov. 14, 2019

Related U.S. Application Data

(63) Continuation of application No. 15/744,477, filed as application No. PCT/US2016/042593 on Jul. 15, 2016, now Pat. No. 10,414,475.
(Continued)

(51) Int. Cl.
B63C 9/18 (2006.01)
B63C 9/125 (2006.01)
(Continued)

(52) U.S. Cl.
CPC ............... *B63C 9/18* (2013.01); *A41D 7/00* (2013.01); *A61B 5/389* (2021.01); *A61B 5/4094* (2013.01); *A61B 5/6804* (2013.01); *B63C 9/1255* (2013.01)

(58) Field of Classification Search
CPC .......... B63C 9/18; B63C 9/1255; A41D 7/00; A61B 5/0488; A61B 5/1094; A61B 5/6804
See application file for complete search history.

(56) References Cited

U.S. PATENT DOCUMENTS 2,996,986 A 8/1961 Wedding
3,345,657 A 10/1967 Peeler
(Continued)

FOREIGN PATENT DOCUMENTS

EP 2 044 922 A2 4/2009
WO 2006134359 A1 12/2006
WO 2015087330 A1 6/2015

OTHER PUBLICATIONS

C. Lausted, et al. "Maximum static inspiratory and expiratory pressures with different lung volumes", BioMedical Engineering OnLine, BioMed Central, 2006, 5:29, pp. 1-6.
(Continued)

*Primary Examiner* — Stephen P Avila
(74) *Attorney, Agent, or Firm* — Thomas|Horstemeyer, LLP

(57) ABSTRACT

In one embodiment, a personal flotation device that can be worn by a user includes an inflation system including an inflatable bladder, a gas-generating component configured to
(Continued)

generate gas using a chemical reaction and inject the generated gas into the bladder to inflate it, and an actuator configured to activate the gas-generating component; a sensor configured to sense one or more physiological parameters of the user; and an inflation control system configured to receive physiological parameter data from the sensor, to determine whether or not the user is experiencing a medical event that places the user at risk of drowning, and, if the user is experiencing such a medical event, to signal the actuator to activate the gas-generating component so as to provide floatation to the user.

18 Claims, 7 Drawing Sheets

Related U.S. Application Data

(60) Provisional application No. 62/192,841, filed on Jul. 15, 2015.

(51) Int. Cl.
  *A61B 5/389* (2021.01)
  *A41D 7/00* (2006.01)
  *A61B 5/00* (2006.01)

(56) References Cited

U.S. PATENT DOCUMENTS

| | | | |
|---|---|---|---|
| 5,013,271 | A | 5/1991 | Bartlett |
| 5,286,462 | A | 2/1994 | Olson |
| 5,941,752 | A | 8/1999 | Liebermann |
| 6,381,482 | B1 | 4/2002 | Jayaraman et al. |
| 6,659,825 | B2 * | 12/2003 | Foss ............... B63C 9/155 441/123 |
| 6,843,694 | B2 | 1/2005 | Simmons |
| 6,970,731 | B1 | 11/2005 | Jayaraman et al. |
| 8,562,524 | B2 | 10/2013 | Osorio |
| 8,715,024 | B2 | 5/2014 | Westwood |
| 2008/0266118 | A1 | 10/2008 | Pierson et al. |
| 2009/0124870 | A1 * | 5/2009 | Arends ............ A61B 5/1112 600/301 |
| 2009/0280705 | A1 | 11/2009 | Puls et al. |
| 2012/0083700 | A1 * | 4/2012 | Osorio .............. A61B 5/11 600/483 |
| 2013/0012830 | A1 * | 1/2013 | Leininger ........ A61B 5/746 600/546 |
| 2014/0273678 | A1 | 9/2014 | Meyer |

OTHER PUBLICATIONS

Milic-Emili J, Orzalesi MM, Cook CD, Turner JM., "Respiratory thoraco-abdominal mechanics in man", J Appl Physiol. 1964;19: 217-223.
Material Safety Data Sheet Calcium hydroxide MSDS, Science Lab.com—Chemicals & Laboratory Equipment, Web14 Apr. 2015. <.sciencelab.com%2Fmsds.php%3Fmsdsld%3D9927122>, 6 pages.
Material Safety Data Sheet Calcium hydride MSDS, Science Lab. com—Chemicals & Laboratory Equipment,Web. Apr. 14, 2015. <.http://www.sciencelab.com/msds.php?msdsld=9927121>, 5 pages.
"All You Need to Know about Wetsuits". IDentex Blog. N.p., Aug. 18, 2013. Web. Apr. 27, 2015. <https://identex.wordpress.com/2013/08/18/wetsuits/>, 5 pages.
"Polyethylene." Wikipedia. Wikimedia Foundation, N.D. Web. Apr. 27, 2015. <http://en.wikipedia.org/wiki/Polyethylene>. 15 pages.
De Dear, R.J., et al., "Convective and radiative heat transfer coefficients for individual human body segments". <http://www.ncbi.nlm.nih.gov/pubmed/9195861> Int J Biometeorol (1997) 40:141-156.
Van de Vel, Anouk, et al., "Non-EEG seizure-detection systems and potential SUDEP prevention: State of the art." Seizure 22 (2013): 345-355.
"Co2 Cartridges—Co2 16g Threaded—Box of 5." Co2 16g Threaded—Box of 5. Co2Cartridges, Web. Apr. 28, 2015. <http://www.co2cartridges.co.uk/index.php?act=viewProd&productId=235>, 2 pages.
"CURE Epilepsy: About Epilepsy: What Is Epilepsy." CURE Epilepsy: About Epilepsy: What Is Epilepsy. Citizens United for Research in Epilepsy, n.d. Web. Apr. 28, 2015. <http://www.cureepilepsy.org/aboutepilepsy/facts.asp>, 4 pages.
Peak Analysis. Web. Apr. 28, 2015. <http://www.mathworks.com/help/signal/examples/peak-analysis.html>, 9 pages.
"Prevalence of Self-Reported Physically Active Adults—United States, 2007" Centers for Disease Control and Prevention. Centers for Disease Control and Prevention, Dec. 3, 2008. Web. Apr. 2, 2015. <http://www.cdc.gov/mmwr/preview/mmwrhtml/mm5748a1.htm>, 5 pages.
"How Much Does Business Insurance cost?" Business Insurance Cost. Average Price. Consumer Agent Portal, Jan. 1, 2015. Web. Apr. 3, 2015. <https://www.trustedchoice.com/business-insurance/compare-coverage/cost/>, 6 pages.
"Information about MDUFA III", Medical Devices. US Food and Drug Administration, Sep. 30, 2014. Web. Apr. 14, 2015. <http://www.fda.gov/MedicalDevices/DeviceRegulationandGuidance/Overview/MDUFAIII/ucm313673.htm>, 3 pages.
Conradsen, lsa, Mihai Moldovan, Poul Jennum, Peter Wolf, Dario Farina, and Sándor Beniczky, "Dynamics of Muscle Activation during Tonic-clonic Seizures." Epilepsy Research (2013) 104: 84-93.
"FICA & SECA Tax Rates." Social Security and Medicare Tax Rates. US Social Security Administration, Apr. 18, 2013. Web. Apr. 14, 2015. <http://www.ssa.gov/oact/progdata/taxRates.html>, 2 pages.
"Epilepsy." Media Centre. World Health Organization, Jan. 1, 2015. Web. Apr. 14, 2015. <http://www.who.int/mediacentre/factsheets/fs999/en/>, 6 pages.
Kong, V.C.Y., D.W. Kirk, F.R. Foulkes, and J.T. Hinatsu. "Development of Hydrogen Storage for Fuel Cell Generators II: Utilization of Calcium Hydride and Lithium Hydride." International Journal of Hydrogen Energy 28 (2003) 205-214.
Pecar, Darja, and Andreja Gorsek. "Kinetic Parameters Determination Using Reaction Calorimetry: Study of Sodium Benzoate Synthesis" David Publishing J. Chem. Chem. Eng. 5 (2011) 89-94.
Wong, Stephanie T. "Computer-aided Modeling of Controlled Release through Surface Erosion with and without Microencapsulation." Scholar Commons. University of South Florida, 2007, pp. 1-155.
Zogg, Andreas, et al., "Isothermal Reaction Calorimetry as a Tool for Kinetic Analysis." Thermochimica Acta 419 (2004) 1-17.
Bradstreet, Kailee. "The 2015 Swimwear Market Trend Report." Transworld Business RSS. The Enthusiast Network, Jan. 4, 2015. Web. Apr. 8, 2015. <http://business.transworld.net/152894/features/2015-swimwear-market-trend-report/>. 9 pages.
"Hazardous Substance Fact Sheet—Calcium Hydroxide." New Jersey Department of Health and Senior Services, Jun. 2005. 6 pages.
Cohen, Marshal. "Innovation, Style & Versatility Drive Swimwear Growth." Total Swimwear Sales. NPD, 2014, Web. Apr. 26, 2015. <https://www.npd.com/wps/portal/npd/us/news/press-releases/innovation-style-and-versatility-drive-swimwear-growth/>, 3 pages.
Köhler, Bert-Uwe, et al. "The Principles of Software QRS Detection", Reviewing and Comparing Algorithms for Detecting this Important ECG Waveform, IEEE Engineering in Medicine and Biology, Jan./Feb. 2002, pp. 42-57.
Evan Ticknor, "An Analysis Into EMG Detection Algorithms", USF Department of Chemical and Biomedical Engineering, INFLATECH, Apr. 2015 pp. 1-13.
International Search Report for PCT/US2016/042593 dated Sep. 23, 2016.

\* cited by examiner

GAS-INFLATABLE PERSONAL FLOTATION DEVICES

CROSS-REFERENCE TO RELATED APPLICATIONS

This application is a continuation application of U.S. Non-Provisional application entitled "Gas-Inflatable Personal Flotation Devices," having Ser. No. 15/744,477 and filed Jan. 12, 2018 which claims priority to 35 U.S.C. § 371 national stage application of PCT Application No. PCT/US2016/042593, filed Jul. 15, 2016, where the PCT claims priority to U.S. Provisional Application Ser. No. 62/192,841, filed Jul. 15, 2015, which are herein incorporated by reference in their entireties.

BACKGROUND

Swimming and water sports are very popular activities. Many people are unable to participate in these activities, however, due to medical conditions, such as epilepsy and other neurological conditions, which put them at risk of drowning. While such individuals could wear conventional flotation devices, such as foam vests or inflated vests or arm cuffs, such devices interfere with water activities. For example, such devices are typically cumbersome and hinder body motion, and further make swimming difficult, particularly under water. While inflatable vests, such as those that use carbon dioxide cartridges, are available on the market, they must be manually activated to inflate. Unfortunately, the user may not be able to activate the vest when the user is experiencing a medical emergency, such as a seizure.

From the above discussion, it can be appreciated that it would be desirable to have a personal flotation device that can provide buoyancy to an individual experiencing a medical event, such as a seizure, which does not interfere with normal water activity in which the individual is participating and which does not require the individual to activate.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a personal flotation device that can provide buoyancy to an individual experiencing a medical event, such as an epileptic seizure, which does not interfere with normal water activity in which the individual is participating and which does not require the individual to activate. Disclosed herein are embodiments of such devices, which can be integrated with a swimming garment, such as a recreational or competitive swimming shirt. The personal flotation device comprises an inflatable bladder that can be inflated by an inflation system under the control of an inflation control system. In some embodiments, the inflation system uses a chemical reaction to generate gas that rapidly fills the bladder to provide buoyancy to the user. In some embodiments, the inflation control system automatically activates the inflation system in response to a determination that the user is having a medical event, such as an epileptic seizure. In some embodiments, this determination is made by sensing and analyzing skeletal muscle contractions of the user.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
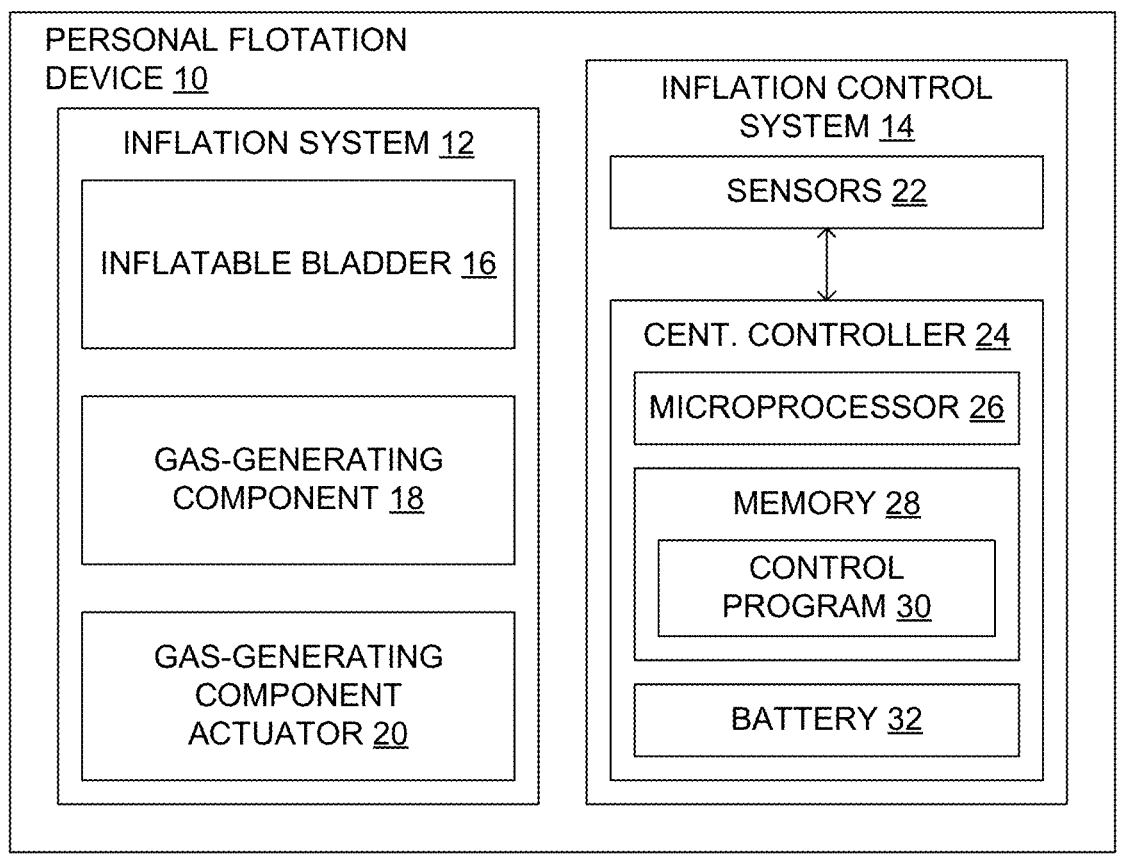
FIG. 1 is a block diagram of an embodiment of a flotation device.

FIG. 1 illustrates the primary components of a personal flotation device 10 that can be worn by a user. In some embodiments, the flotation device 10 can be used as an independent device separate from a swimming garment. In other embodiments, the flotation device 10 can be used with a swimming garment, such as a swimming shirt. In the latter case, the flotation device 10 can be integrated into the garment during its manufacture or added to the garment afterward in a retrofitting scenario.

As shown in FIG. 1, the flotation device 10 generally comprises an inflation system 12 and an inflation control system 14. The inflation system 12 includes an inflatable bladder 16 that can be rapidly filled with a gas to provide buoyancy to the device user. The gas that fills the bladder 16 is produced by a gas-generating component 18. As described below, the gas-generating component 18 can, in some embodiments, generate gas through a chemical reaction that occurs when the gas-generating component is activated by a gas-generating component actuator 20.

The inflation control system 14 includes one or more sensors 22 that can be used to sense one or more physiological parameters of the user that can be indicative of a medical event that places the user at risk of drowning. As described below, the sensors 22 can, in some embodiments, comprise electrodes that are placed on the user's skin on particular parts of the body and used to sense the user's muscle contractions. The sensors 22 are in electrical communication with a central controller 24 of the flotation device 10 that is used to control activation of the actuator 20. More particularly, the central controller 24 is configured to activate the actuator 20 when the parameters sensed by the sensors 22 are indicative of a medical event occurring.

As shown in FIG. 1, the central controller 24 can include a microprocessor 26, memory 28 (which can optionally be integrated into the microprocessor), and a battery 32. Stored within the memory 28 (a non-transitory computer-readable medium) is a control program 30 that can be executed by the microprocessor 26 to determine when the actuator 20 should be activated. The control program 30 comprises one or more algorithms (computer logic and executable instructions) configured to analyze the data collected by the sensors 22 and determine whether or not a medical event is occurring. If it is determined that such a medical event is occurring, the microprocessor 26 can send a signal to the gas-generating component actuator 20 to activate it and cause the gas-generating component 20 to inflate the bladder 16.

In some embodiments, the flotation device 10 can be specifically configured for use by persons who have epilepsy and, therefore, suffer from epileptic seizures that put them at risk of drowning when participating in water activities. In such an application, the device 10 can be configured to detect the onset of an epileptic seizure and, in response, immediately inflate to prevent drowning. One way in which such seizures can be detected is by capturing and analyzing electromyography (EMG) signals from the user's muscles. EMG signals measure the motor neuron action potential in skeletal muscles. Because seizures involve involuntary strong and rapid contractions of the skeletal muscles that do not normally occur during normal movement or exercise, signals that identify such contractions can provide an indication of when the user is having a seizure. The EMG signals can be collected with the sensors 22, in the form of EMG electrodes that are placed on the skin surface. These signals can be provided to the central controller 24 and analyzed by executing the control program 30, which can be specifically configured to identify contractions indicative of an epileptic seizure.

Experiments were performed to determine which muscle groups are best for use detecting epileptic seizures using EMG. In these experiments, subjects simulated swimming movements as well as muscle contractions of the type that result when an epileptic seizure occurs. It was found that EMG signals obtained from the pectoralis major and bicep muscles provide signals that most clearly identify the seizure-like contractions. After these initial findings, additional testing was performed with a focus on these targeted areas. With two subjects performing swimming activities and simulated seizures, the data collected via EMG was uploaded to MATLAB and stored as a single array of voltage values. Qualitative analysis indicated that most of the predicted seizures were due to large changes in amplitude and an increase in the frequency of waves in the range of these increased amplitudes. Taking this information as a genesis for quantitative analysis, a MATLAB program was created to examine these observations. The effectiveness of this post-processing technique determined the viability of seizure detection through EMG in the bicep and pectoral muscles.

Figure 2:
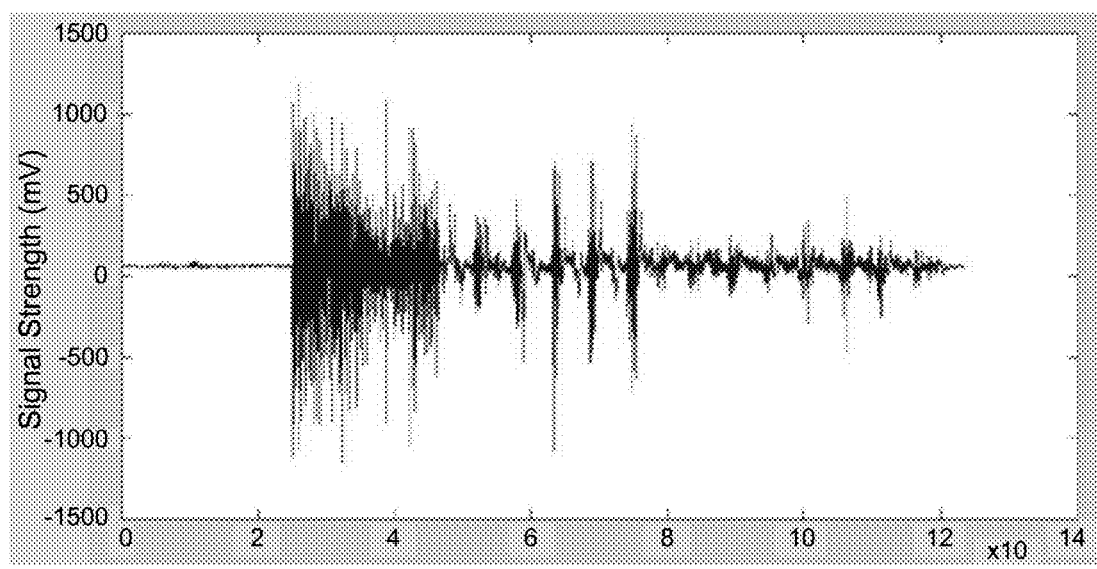
FIG. 2 is a graph that plots motor neuron action potential activity of a subject as sample point versus signal strength (mV).
Figure 3:
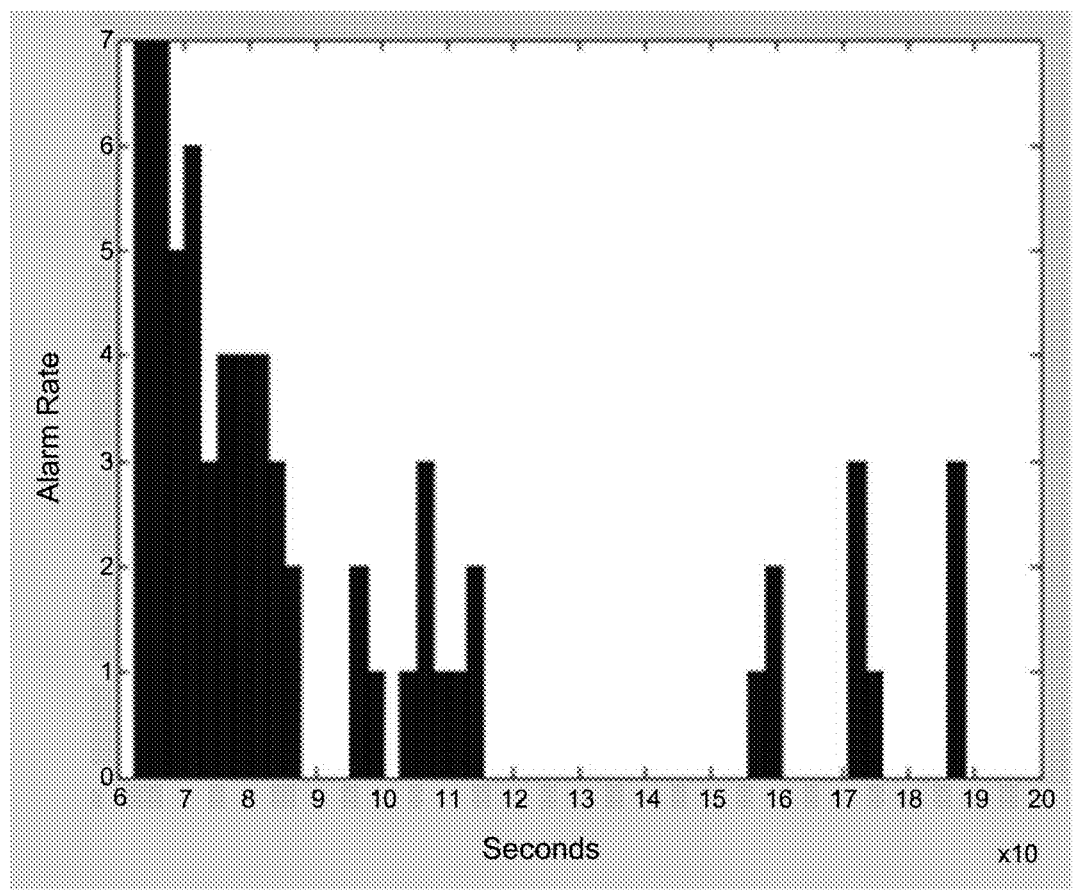
FIG. 3 is a histogram that shows the frequency at which local maxima in the data of FIG. 2 reached amplitude thresholds.

As a preliminary examination into the characteristics of the data set, all of the activities of an initial subject were captured via a forearm EMG electrode were combined into a single data set and plotted. In this case, the data was plotted as sample point versus signal strength (mV), as shown in FIG. 2. It was apparent from this graph that a majority of the waves in the seizure portion of the data set exceeded 500 mV. The next step was to determine what the distribution looked like for signals that reached above this 500 mV envelope. A simple program was created to identify all of the local maxima in the data set that had at least a 40 sample separation between other peaks and was at least 500 mV in strength. Sample location values were divided by 4000 to yield final results in seconds. The data collection system ran at 4000 samples/sec. Finally, a histogram (FIG. 3) was created to show the frequency at which local maxima were reaching these amplitude requirements.

It is apparent from the histogram that amplitude analysis would see significant consideration given the overwhelming frequency in the seizure portion. The histogram also shows small rates falling outside of the seizure portion of the data. Given this dynamic, the program would still need to mitigate the chance of a false positive reading by minimizing the effects of these outliers.

To determine the capability for the program to recognize seizures while also mitigating the chance for false positives, all of the activities for a particular muscle group were combined to form a single continuous array. After forming a single data array, an envelope requirement was created based on a statistical analysis of the local maxima in the data. Using a MATLAB peak finder, finding every maximum that is at least 40 data points from the last maxima, an average and standard deviation was taken over all of those peaks. A separation of at least 40 samples was used to minimize the effects of outliers in the data set caused by movement of the electrodes or erratic movements during testing. An envelope was then calculated based off of the mean and standard deviation. This automated envelope helped determine the minimum size before a peak becomes significant in determining whether a seizure is occurring. Multiple envelope values were tried and it was found through continuous testing that one standard deviation above the mean peak value would yield the most accurate results.

The same automated peak finder was utilized again. However, the additional minimum peak size requirement was added to isolate only those peaks above a particular size and separation. From this data set, each peak value contained its peak size and location in the data set. From these location values, a new variable pkint (peak interval) was created by finding the separation between peak locations. An additional value of zero was added to the beginning of the data set for general indexing and matrix formatting purposes.

The number of elements in the pkint array were counted. Two important variables were then created. A two-columned warning matrix was formed to dictate whether an area of the overall data set would begin to indicate a seizure occurring. This was determined by piecing together a picture of each data point and the area previous to said data point. During each iteration of the program, an average was taken for each new data point that includes the previous nine values. This average represents the average separation between peaks above the minimum envelope over a set of ten peaks. A logic operator was used to determine if the average of each set was less than 250 data points per peak. If the average was less than 250, a value of 1 was assigned to the corresponding data point. Otherwise, the data point was assigned a 0.

This introduces the next significant variable, the initiate. The initiate variable is a counter that indicates to the device to initiate the inflation sequence. Each time a warning value is assessed a value of 1, the initiate counter increases by 1. In the case that the warning value is a 0, the initiate counter is decreased by 1. The counter cannot fall below the value 0. In the event that the counter reaches a value of 5, the counter resets and an inflate determination is reached.

Figure 4A:
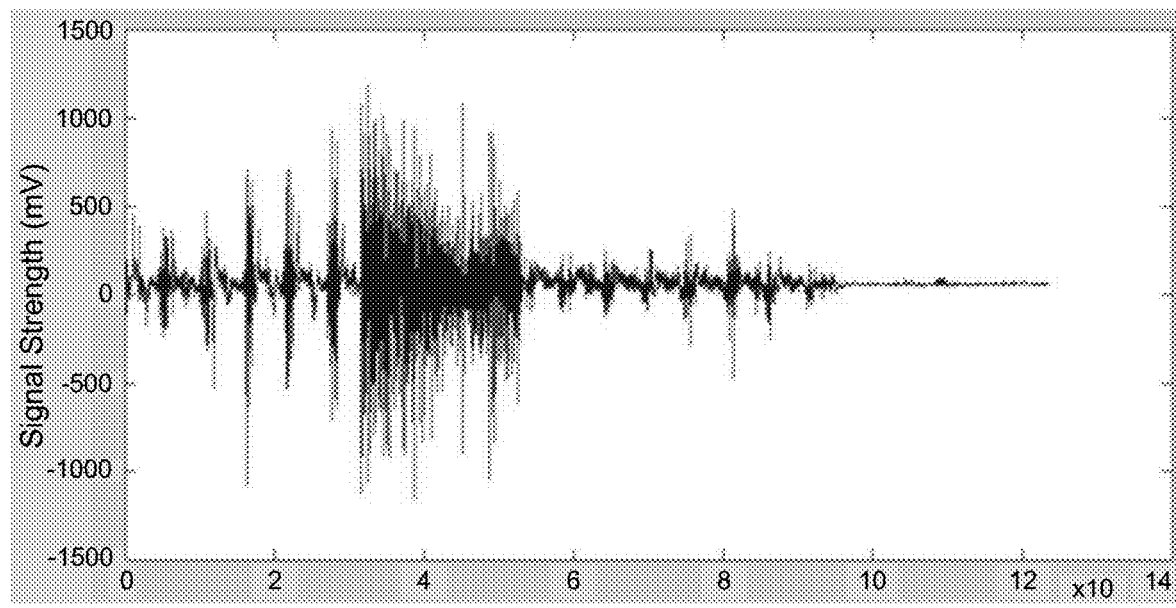
FIG. 4A is a data set for a first subject comprising a graph that plots the subject's motor neuron action potential activity and a table that identifies detected seizures.
Figure 4B:
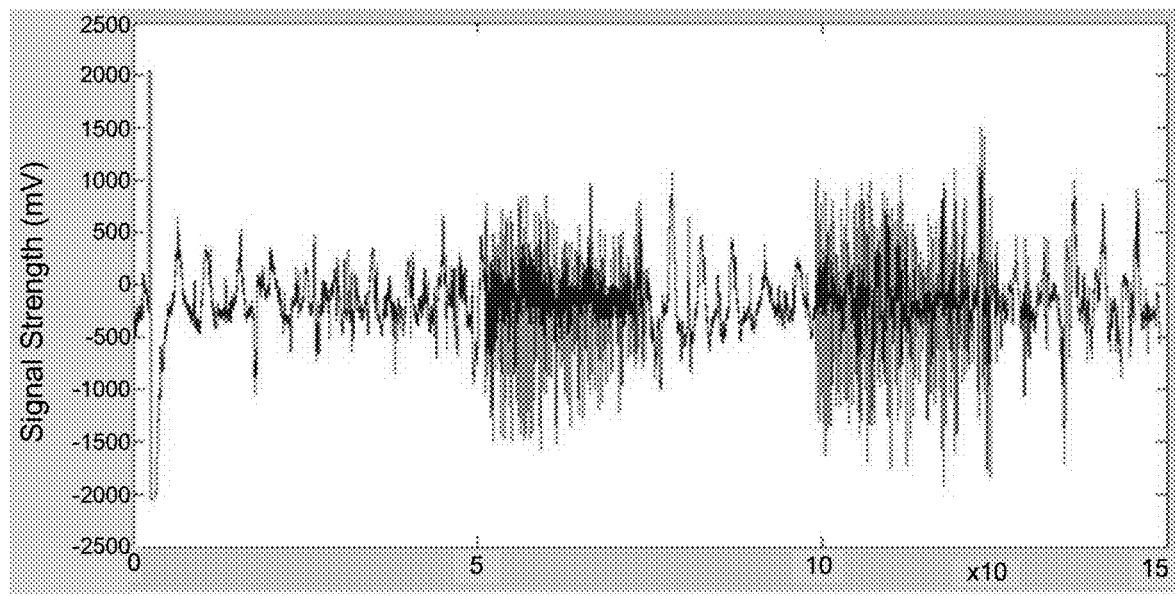
FIG. 4B is a data set for a second subject comprising a graph that plots the subject's motor neuron action potential activity and a table that identifies detected seizures.

With two different test subjects having provided data for the same activities, the program was then evaluated. The effectiveness of the MATLAB code was governed by two principles: (a) detect a seizure within (certain time frame) seconds and (b) eliminate all false positives. All data sets were tested in various orders of activity and reached similar results. FIGS. 4A and 4B illustrate two data sets from two different test subjects, respectively, and show the capability of the program. The first data set (FIG. 4A) shows a very visible distinction between swimming motions, a baseline, and a seizure. The second data set (FIG. 4B) shows activities performed that are less distinguishable from one to another.

Comparing the two data sets, false positives were absent in both, but the less distinguishable the seizure was from activities, the less often the system recognized seizures. However this was not seen as a major issue, as even in the second data set the seizure was detected approximately once every second.

The above-described findings confirm both that the amplitude and frequency of the EMG signals obtained from the bicep and/or pectoral region can be used to detect epileptic seizures and, therefore, can be used to determine when to trigger inflation of the flotation device 10. Accordingly, in some embodiments, the control program 30 can be configured to analyze EMG signals collected by the sensors 22 and determine from the amplitude and frequency of those signals whether or not the user is having an epileptic seizure. For example, if a threshold number of contractions that exceed a predetermined amplitude threshold are detected within a predetermined period of time, it can be concluded that the user is having a seizure. In such a case, the microprocessor 26 can activate the actuator 20 to cause the gas-generating component 18 to fill the bladder 16 with gas.

In some embodiments, the flotation device 10 can be specifically calibrated for each particular user. In such cases, a calibration process can be performed during which the user performs particular physical activities while the flotation is connected to the body to enable the central controller 24 to store data in memory 28 that will be used in the seizure determination. These activities serve as a safe means to accurately calibrate the controller 24 to each individual user. By way of example, the activities can be conducted out of the water and comprise mimicking freestyle swimming, mimicking breast-stroke, mimicking treading water, full-body tensing (to calibrate maximal voluntary contraction), and sitting in a relaxed position (to calibrate baseline muscle activity).

As noted above, the gas-generating component 18 can generate gas through a chemical reaction. In some embodiments, the chemical reaction can utilize a hydrogen-generating compound that generates hydrogen gas. One example of a hydrogen-generating compound is calcium hydride (CaH$_2$), which reacts with water to create calcium oxide and hydrogen gas:

$$CaH_2 + 2H_2O \rightarrow Ca(OH)_2 + 2H_2 \quad \text{[Equation 1]}$$

The kinetics of the calcium hydride/water reaction was investigated. Calculations were performed to determine the water requirements to properly feed the reaction. An experimental amount of approximately 0.1 gram calcium hydride was mixed with water in four trials. Two trials were performed at 25° C. and two trials were performed at 30° C. The two trials performed at the same temperatures had different amounts of calcium hydride on the order of +/−0.025 grams approximately. Calcium hydride was placed in a small reaction vial, which was lowered into a calorimeter. The calorimeter reached steady state conditions and proper temperature values. Next, 3 grams of distilled water (3 mL) was injected into the reaction vial. In order to minimize pressure build up, a vent was placed in the top of the reaction vial to vent the hydrogen gas. Once the water was injected, the reaction was monitored until values returned to the steady state conditions of the system. With the four trials completed, kinetic data was calculated for the reaction of calcium hydride with water.

Figure 5:
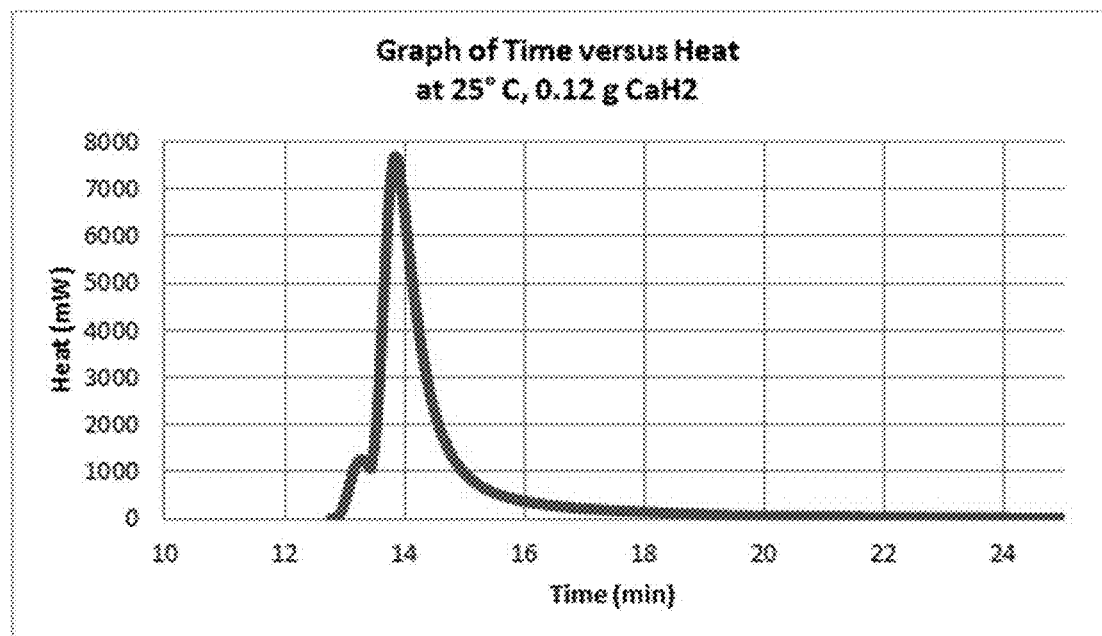
FIG. 5 is a graph that plots heat versus time for a gas-generating reaction.
Figure 6:
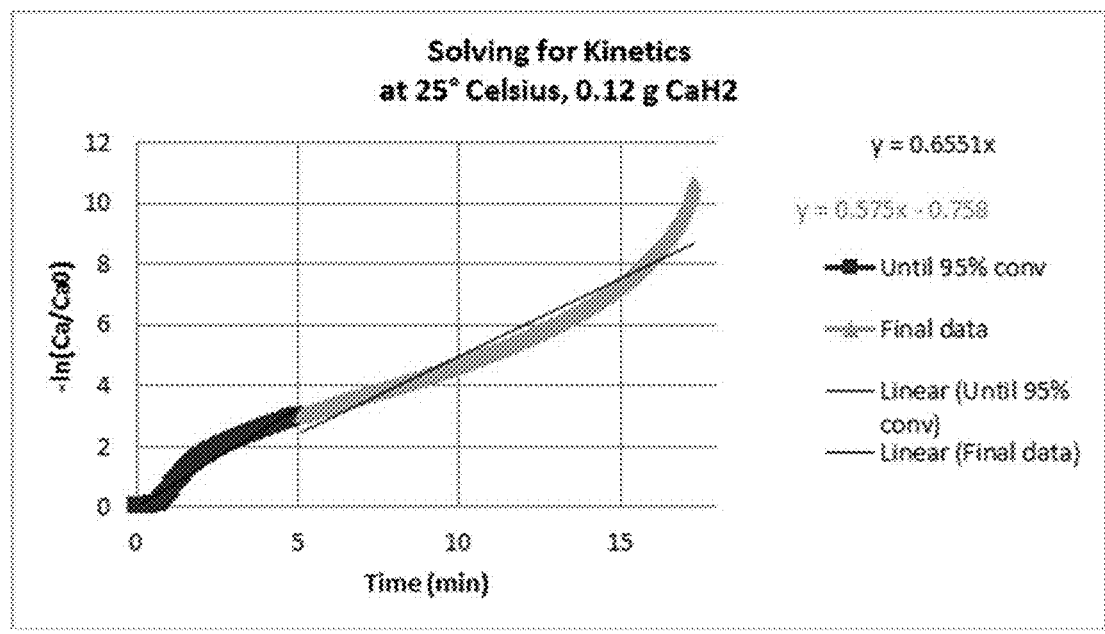
FIG. 6 is an illustration of an example of a graphical method for solving the kinetics of the reaction of FIG. 5.

FIG. 5 shows the results from the calorimeter testing performed at 25° C. with 0.12 gm of calcium hydride reacting. FIG. 6 shows an example of a graphical method for solving the kinetics. Table 1 shows the k values calculated for each trial and the time it took for each trial to reach 95% conversion. Based on the information gathered from experimentation, the average k value was 0.576 min$^{-1}$. The reaction is pseudo-first order due to the excess water utilized to quench the reaction. The results of testing suggest that the reaction is highly independent of temperature and therefore has low activation energy. The time for the reaction to occur was minimal. This experimentation confirmed that calcium hydride is a viable option for use in the gas-generating component 18 and for inflation of the bladder 16.

TABLE 1

Final Kinetic Data

| Temperature (° C.) | Amount CaH$_2$ (g) | K value | Time to Reach 95% conversion |
|---|---|---|---|
| 25 | 0.120 | 0.655 | 5.10 min |
| 25 | 0.114 | 0.665 | 4.72 min |
| 30 | 0.123 | 0.529 | 6.15 min |
| 30 | 0.154 | 0.454 | 7.35 min |

In addition to providing buoyancy to the user, the flotation device 10 must also not harm the user. The calcium hydride/water reaction is an exothermic reaction ($\Delta H_{R \times n}$=−249.72 kJ/mol). Therefore, it is important to insure that the user of the device 10 is not burned upon inflation. The amount of calcium hydride needed for inflation can be calculated from the amount of pressure of hydrogen gas required to provide buoyancy to the user. In some embodiments, 34 lbf of buoyancy is provided to comply with U.S. Coast Guard life jacket standards. In such a case, approximately 5 gm of calcium hydride is needed. An amount of water in excess of that needed for the reaction can be used to quench the reaction and absorb much of the generated heat.

With this in mind, it was determined to charge the vessel with approximately 10 times the stoichiometric amount of water (50 mL) required for the 5 gm of calcium hydride. Next, a simple energy balance was used:

$$Q_{R \times n} = Q_w + Q_p = m \Delta H = m C_p \Delta T \quad \text{[Equation 2]}$$

This equation states that the heat produced by the reaction ($Q_{R \times n}$) is equal to the heat used to get the water to boiling point ($Q_w$) plus the heat used for phase change ($Q_p$). With 5 gm of calcium hydride, the reaction will produce approximately 30 kJ of energy. This is enough energy to take the water to 100° C. and partially into the two-phase region. This high temperature should be kept in mind when designing the gas-generating component 18 and determining its location relative to the user's body.

Hydrogen has a very low heat capacity. It therefore is not likely to carry much of the heat produced by the reaction that occurs in the gas-generating component 18 into the bladder 16. However, if a significant amount of steam, which has a much higher heat capacity, is produced, this steam could carry a significant amount of heat into the bladder 16. Assuming the final quality of the system is approximately 11%, about 0.3 moles of water would be turned into steam. However, the drastic change in volume that would occur during filling of the bladder 16 would cause most, if not all, of the steam to condense. Therefore, the heat of the reaction is less of a concern for the bladder 16.

Figure 7A:
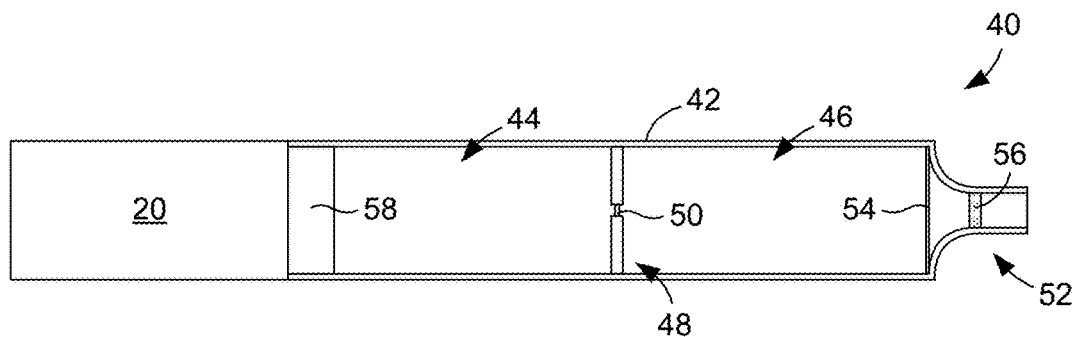
FIGS. 7A-7C are drawings of an embodiment of a gas-generating component in various stages of activation.
Figure 7B:
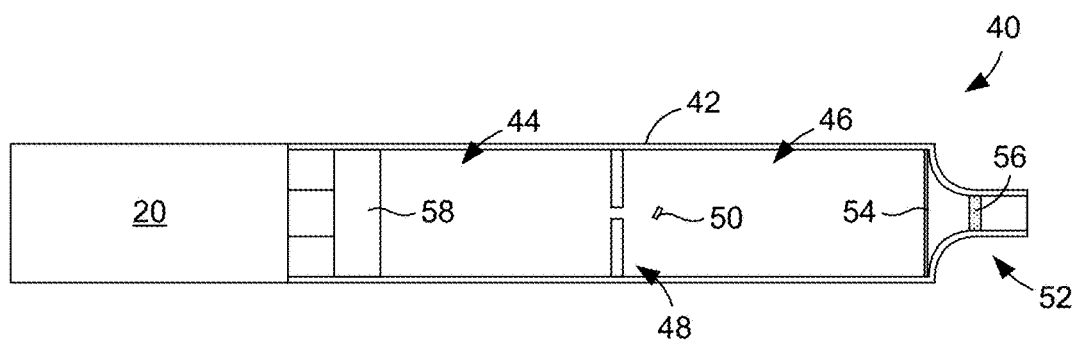
Figure 7C:
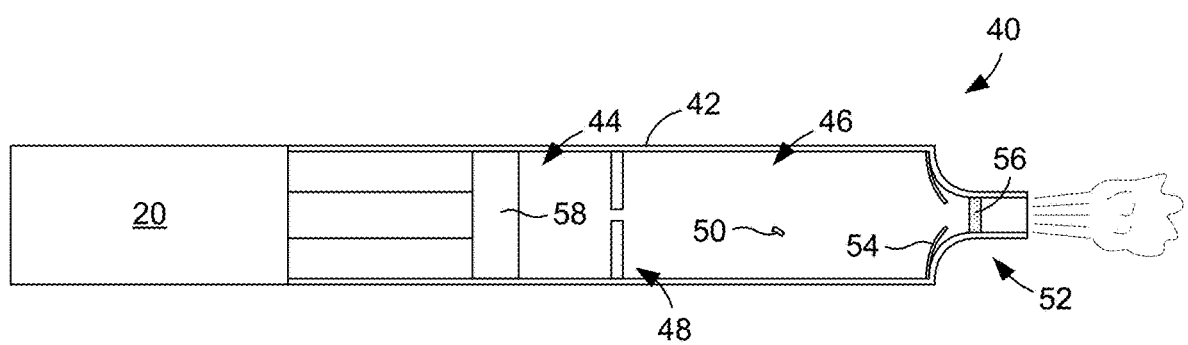

FIGS. 7A-7C illustrate an embodiment of a gas-generating component 40 that can be used in the flotation device 10. As indicated in these figures, the component 40 comprises a sealed, rigid outer housing 42 that defines an interior space that is divided into a first compartment 44 and a second compartment 46 by a divider wall 48. In some embodiments, the housing 42 is made of a polymeric material having good heat insulating properties, such as polycarbonate. The housing 42 can have dimensions that enable the gas-generating component 40 to be unobtrusive to the user when participating in water activities. The two compartments 44, 46 are configured to contain water and a gas-generating compound (e.g., calcium hydride), respectively, in amounts appropriate for generating a volume of gas that will rapidly fill the bladder.

As shown in FIG. 7A, the divider wall 48 incorporates a first sacrificial element 50 that will break when a predetermined amount of pressure is applied to the portion to enable the water and the gas-generating compound to mix. By way of example, the sacrificial element 50 can comprise a weak point in the wall or a relatively weak member, such as a thin membrane, that is incorporated into the wall.

With further reference to FIG. 7A, the gas-generating component 40 further includes an exit nozzle 52 through which gas generated by the reaction between the water and the gas-generating compound can escape the component and be injected into the bladder 16. As shown in the figure, a second sacrificial element 54, such as a thin membrane, separates the nozzle 52 from the second compartment 46. This sacrificial element 54 is designed to break a when the generated gas applies a predetermined amount of pressure. In some embodiments, the nozzle 52 includes a filter 56 that prevents the sacrificial elements 50, 54 and the reactants from passing into the bladder 16.

As described above, the gas-generating component 40 is activated by the gas-generating component actuator 20. In some embodiments, the actuator 20 applies pressure to the water contained in the first compartment 44. As illustrated in FIG. 7B, this pressure can be applied, for example, using a piston 58 that is driven into the gas-generating component 18 by the actuator 20. This pressure is transferred by the water to the first sacrificial element 50 so as to cause it to break or detach from the divider wall 48, as shown in FIG. 7B.

Once the first sacrificial element 50 has broken or has been detached, the water, under the pressure applied by the actuator 20, enters the second compartment 46 and mixes with the gas-generating compound contained therein. The water and the gas-generating compound react with each other and rapidly produce a substantial volume of gas, such as hydrogen gas. As this gas is produced, it exerts pressure on the second sacrificial element 54 to cause it to break, as shown in FIG. 7C. This enables the gas to escape the second compartment 46 and the gas-generating component 40, and inflate the bladder 16.

While a particular physical configuration for the gas-generating component 18 has been illustrated in FIG. 7 and described above, it is noted that the physical details of this configuration are not critical. Instead, the functionality provided by the component 18 (i.e., separately containing water and a gas-generating compound, enabling the water and gas-generating compound to mix, and enabling gas generated from the reaction between the water and gas-generating compound to fill the bladder 16) is was is important. Accordingly, it will be appreciated that any physical configuration that can provide such functionality can be used for the gas-generating component 18.

Figure 8B:
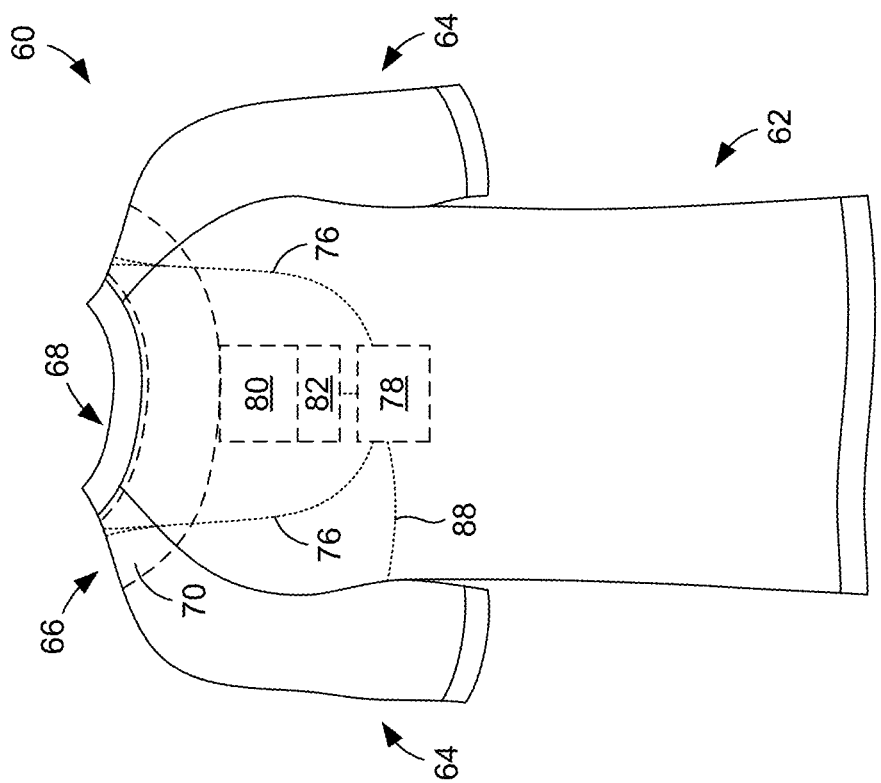
FIGS. 8A and 8B are front and back views, respectively, of an embodiment of a swimming garment that incorporates a flotation device.
Figure 8A:
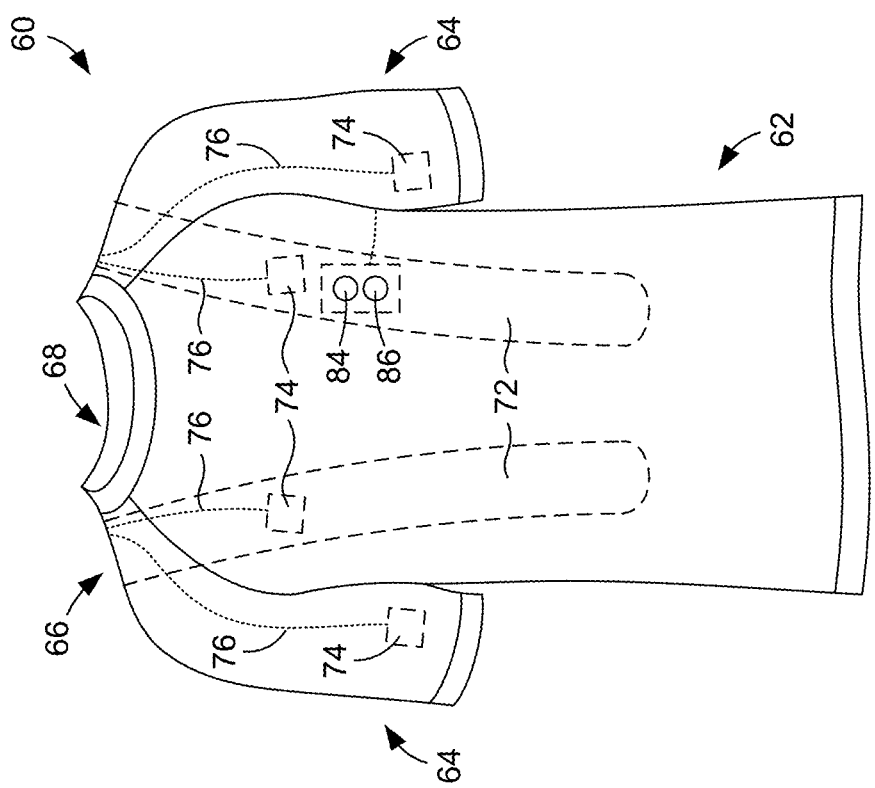

As noted above, the flotation device 10 can be integrated with a swimming garment, such as a swimming shirt. FIGS. 8A and 8B illustrate an embodiment of such a shirt 60. As shown in these figures, the shirt 60 generally comprises a body 62 and sleeves 64 that are attached to the body. The shirt body 62 is generally configured to cover the user's torso, while the shirt sleeves 64 are generally configured to cover the user's upper arms. While short sleeves are illustrated in FIGS. 8A and 8B, it is noted that the sleeves 64 can alternatively be long sleeves that cover the user's entire arms. The body 62 and sleeves 64 can be made of any suitable materials. In some embodiments, they are made of synthetic elastic materials that do not interfere with the user's mobility while worn in the water. By way of example, the body 62 and sleeves 64 can be made of a neoprene material, which can be approximately 1 to 2 mm thick. When neoprene is used, the shirt 60 inherently provides insulation to the user from the heat generated by the flotation device 10.

As shown in the figures, the shirt 60 incorporates the various components of the flotation device 10. These components include an inflatable bladder 66. In the embodiment of FIG. 8, the bladder 66 has a yoke-like design in which the bladder comprises a continuous, elongated, tubular element that extends around the back of the shirt collar 68 (see FIG. 8B) and down the front of the shirt 60 on both sides of the user's body (see FIG. 8A). More particularly, the bladder 66 has a neck portion 70 that extends from one lateral side of the collar 68, around the back of the collar, and to the other lateral side of the collar, and two opposed elongated torso portions 72 that each extends down from the neck portion along the front of the shirt 60 so as to extend across the user's chest and stomach on either side of the user's sagittal plane when the shirt is worn. In some embodiments, the bladder 66 can be made of polyurethane coated nylon. As indicated by dashed lines, the bladder 66 can be integrated into the material of the shirt body 62. For example, the bladder 66 can be sewn into an internal pocket formed in the shirt body 62 so as to be inconspicuous and hydrodynamic.

With reference to FIG. 8A, the shirt 60 also includes one or more sensors 74 that are placed at strategic positions within the shirt. More particularly, the shirt 60 includes one sensor 74 incorporated into each shirt sleeve 64 at a position at which they will overlie the biceps muscles when the shirt is worn, and two sensors 74 incorporated into the shirt body 62 at positions at which they will overlie the pectoralis muscles when the shirt is worn. Each sensor 74 can comprise an EMG electrode that is affixed (e.g., sewn or glued) to the interior surface of the shirt 62 such that the sensor can make direct contact with the skin of the user. In some embodiments, each sensor 62 can comprise a waterproof foam/gel surface electrode.

Connected to each sensor 74 is an electrical conductor 76, such as an insulated metal wire, that extends from the sensor to the back of the shirt 60 and a central controller 78, which is integrated therewith. Like the bladder 66, the central controller 78 can be can be sewn into an internal pocket formed in the shirt body 62 so as to be inconspicuous and hydrodynamic. As noted above, this central controller 78 can comprise the microprocessor 26, memory 28, and battery 32. In the illustrated embodiment, the central controller 78 is integrated with the shirt body 62 so as to be positioned at the middle or upper back of the user when the shirt is worn.

Also integrated with the back of the shirt body 62 is the gas-generating component 80 and the gas-generating component actuator 82, which is in electrical communication with the central controller 78. The gas-generating component 80 is coupled to the bladder 66 such that the gas generated within the component is ejected into the bladder when it is activated by the actuator 82 under the control of the central controller 78. Like the central controller 78, the gas-generating component 80 and the gas-generating component actuator 82 can be can be sewn into internal pockets formed in the shirt body 62 so as to be inconspicuous and hydrodynamic. In at least the case of the pocket used to contain the gas-generating component 80, the pocket can be opened and closed by the user to remove and replace the gas-generating component once it has been used.

In some embodiments, the shirt 60 and its flotation device can include manual controls that enable the user to determine when the bladder 66 is or is not inflated. As shown in FIG. 8A, an inflation activation button 84 and an inflation cancelation button 86 can be provided on the exterior of the front of the shirt 60 and electrically connected to the central controller 78 with an electrical conductor 88. When provided, the activation button 84 can be pressed by the user to activate the actuator 82 and inflate the bladder 66. In such a case, the inflation device of the shirt 60 can be activated by the user when he or she feels a seizure coming on. More generally, however, the inflation device of the shirt 60 can be used by anyone who wishes to use a manually activated flotation device.

When the cancelation button 86 is provided, it can be pressed by the user to prevent activation of the actuator 82 and inflation of the bladder 66. In such a case, the inflation device can incorporate an auditory and/or vibratory alarm that is activated by the central controller 78 when it determines that the user is having a seizure. The central controller 78 can be configured to delay activation of the actuator 82 for a few seconds after the alarm is initiated, however, to provide the user with an opportunity to override inflation of the bladder 66 in cases in which the user is not actually experiencing a seizure (i.e., a false positive determination has been made by the controller).

The invention claimed is:

1. A personal flotation device adapted to be worn by a user comprising:
    an inflation system including:
        an inflatable bladder,
        a gas-generating component configured to generate gas using a chemical reaction and inject the generated gas into the bladder to inflate it, and
        an actuator configured to activate the gas-generating component;
    a sensor including an electrode configured for application to the user's skin, wherein the sensor is configured to sense contractions of the user's skeletal muscles; and
    an inflation control system configured to receive muscle contraction data from the sensor, to determine whether or not the muscle contractions are indicative of the user experiencing a seizure that places the user at risk of drowning, and, if the user is experiencing a seizure, to signal the actuator to activate the gas-generating component so as to provide buoyancy to the user.

2. The device of claim 1, wherein the gas-generating component comprises separate compartments including a first compartment that contains water and a second compartment that contains a gas-generating compound.

3. The device of claim 2, wherein the gas-generating compound is a hydrogen-generating compound and the gas-generating component is configured to inject hydrogen gas into the bladder.

4. The device of claim 3, wherein the hydrogen-generating compound is calcium hydride.

5. The device of claim 1, wherein the muscle contraction data comprises electromyography (EMG) signals.

6. The device of claim 5, wherein the inflation control system is configured to analyze the EMG signals and signal the actuator when the amplitude and frequency of the signals exceed predetermined thresholds.

7. The device of claim 1, wherein the device is integrated into a swimming garment.

8. A swimming garment configured to prevent drowning of a wearer of the garment, the garment comprising:
    a garment body;
    garment sleeves; and
    a personal flotation device comprising:
        an inflation system including an inflatable bladder, a gas-generating component configured to generate gas using a chemical reaction and inject the generated gas into the bladder to inflate it, and an actuator configured to activate the gas-generating component;
        a sensor including an electrode configured for application to the wearer's skin, wherein the sensor is configured to sense contractions of the wearer's skeletal muscles; and
        an inflation control system configured to receive muscle contraction data from the sensor, to determine whether or not the muscle contractions are indicative of the wearer experiencing a seizure that places the user at risk of drowning, and, if the wearer is experiencing a seizure, to signal the actuator to activate the gas-generating component so as to provide buoyancy to the wearer.

9. The garment of claim 8, wherein the garment body and sleeves are made of neoprene.

10. The garment of claim 8, wherein the inflatable bladder comprises a continuous, elongated, tubular element that extends around a back of a collar of the garment and down a front of the garment.

11. The garment of claim 8, wherein the muscle contraction data comprises electromyography (EMG) signals.

12. The garment of claim 11, wherein the inflation control system is configured to analyze the EMG signals and signal the actuator when the amplitude and frequency of the signals exceed predetermined thresholds.

13. A method for preventing drowning of an individual, the method comprising:
    sensing skeletal muscle contractions of the individual;
    determining whether or not the individual is experiencing a seizure that places the individual at risk of drowning; and
    if the individual is experiencing a seizure, automatically activating a gas-generating component worn by the individual to generate gas using a chemical reaction and inject the generated gas into a bladder also worn by the individual to inflate the bladder and provide buoyancy to the individual.

14. The method of claim 13, wherein sensing skeletal muscle contractions comprises collecting electromyography (EMG) signals.

15. The method of claim 14, wherein determining whether or not the individual is experiencing a seizure comprises analyzing the EMG signals to determine if the amplitude and frequency of the signals exceed predetermined thresholds.

16. The device of claim 1, wherein the inflation control system is configured to determine whether or not the user is experiencing an epileptic seizure.

17. The garment of claim 8, wherein the inflation control system is configured to determine whether or not the wearer is experiencing an epileptic seizure.

18. The method of claim 13, wherein determining whether or not the individual is experiencing a seizure comprises determining whether or not the individual is experiencing an epileptic seizure.

\* \* \* \* \*